United States Patent

Milling

Patent Number: 6,096,698
Date of Patent: Aug. 1, 2000

[54] GLOW IN THE DARK TOILET BOWL DISINFECTANT COMPOSITION

[76] Inventor: Michael Milling, 312 Fairfield St., Winnsboro, S.C. 29180

[21] Appl. No.: 09/288,120

[22] Filed: Apr. 8, 1999

[51] Int. Cl.[7] .................................................. C11D 77/04

[52] U.S. Cl. .......................... 510/191; 510/238; 510/445; 510/446; 510/447; 510/504; 510/100; 252/301.4 R

[58] Field of Search .................................... 510/191, 238, 510/445–447, 504, 100, 192; 252/301.4 R, 301.4 S, 301.4 A

[56] References Cited

U.S. PATENT DOCUMENTS

| | | | |
|---|---|---|---|
| 5,246,631 | 9/1993 | Halbritter | 252/700 |
| 5,427,708 | 6/1995 | Stark | 252/108 |
| 5,689,842 | 11/1997 | Delaney et al. | 4/661 |

*Primary Examiner*—Yogendra Gupta
*Assistant Examiner*—D G Hamlin

[57] ABSTRACT

A glow in the dark toilet bowl disinfectant composition for fluorescently illuminating the water in the toilet bowl. The glow in the dark toilet bowl disinfectant composition includes a water soluble ammonia-based disinfectant combined with amounts of strontium sulfide, barium sulfide, lithium fluoride, samarium oxide and cerium oxide.

4 Claims, 1 Drawing Sheet

GLOW IN THE DARK TOILET BOWL DISINFECTANT COMPOSITION

BACKGROUND OF THE INVENTION

1. Field of the Invention

The present invention relates to toilet bowl disinfectant compositions and more particularly pertains to a new glow in the dark toilet bowl disinfectant composition for fluorescently illuminating the water in the toilet bowl.

2. Description of the Prior Art

The use of toilet bowl disinfectant compositions is known in the prior art. More specifically, toilet bowl disinfectant compositions heretofore devised and utilized are known to consist basically of familiar, expected and obvious configurations, notwithstanding the myriad of designs encompassed by the crowded prior art which have been developed for the fulfillment of countless objectives and requirements.

Known prior art includes U.S. Pat. Nos. 5,427,708; 5,246,631; 5,689,842; 5,730,321; 2,011,732; and U.S. Patent No. Des. 343,642 which are all incorporated by reference herein.

While these patents fulfill their respective, particular objectives and requirements, the aforementioned patents do not disclose a new glow in the dark toilet bowl disinfectant composition. The inventive composition includes a water soluble ammonia-based disinfectant combined with amounts of strontium sulfide, barium sulfide, lithium fluoride, samarium oxide and cerium oxide.

In these respects, the glow in the dark toilet bowl disinfectant composition according to the present invention substantially departs from the conventional concepts and designs of the prior art, and in so doing provides a composition primarily developed for the purpose of fluorescently illuminating the water in the toilet bowl.

SUMMARY OF THE INVENTION

In view of the foregoing disadvantages inherent in the known types of toilet bowl disinfectant compositions now present in the prior art, the present invention provides a new glow in the dark toilet bowl disinfectant composition wherein the same can be utilized for fluorescently illuminating the water in the toilet bowl.

The general purpose of the present invention, which will be described subsequently in greater detail, is to provide a new glow in the dark toilet bowl disinfectant composition and method which has many of the advantages of the toilet bowl disinfectant compositions mentioned heretofore and many novel features that result in a new glow in the dark toilet bowl disinfectant composition which is not anticipated, rendered obvious, suggested, or even implied by any of the prior art toilet bowl disinfectant compositions, either alone or in any combination thereof.

To attain this, the present invention generally comprises a water soluble ammonia-based disinfectant combined with amounts of strontium sulfide, barium sulfide, lithium fluoride, samarium oxide and cerium oxide.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other compositions, methods and systems for carrying out the several purposes of the present invention. It is important, therefore, that the claims be regarded as including such equivalent compositions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new glow in the dark toilet bowl disinfectant composition and method which has many of the advantages of the toilet bowl disinfectant compositions mentioned heretofore and many novel features that result in a new glow in the dark toilet bowl disinfectant composition which is not anticipated, rendered obvious, suggested, or even implied by any of the prior art toilet bowl disinfectant compositions, either alone or in any combination thereof.

It is another object of the present invention to provide a new glow in the dark toilet bowl disinfectant composition which may be easily and efficiently manufactured and marketed.

An even further object of the present invention is to provide a new glow in the dark toilet bowl disinfectant composition which is susceptible of a low cost of manufacture with regard to both materials and labor, and which accordingly is then susceptible of low prices of sale to the consuming public, thereby making such glow in the dark toilet bowl disinfectant composition economically available to the buying public.

Still another object of the present invention is to provide a new glow in the dark toilet bowl disinfectant composition for fluorescently illuminating the water in the toilet bowl.

Yet another object of the present invention is to provide a new glow in the dark toilet bowl disinfectant composition which includes a water soluble ammonia-based disinfectant combined with amounts of strontium sulfide, barium sulfide, lithium fluoride, samarium oxide and cerium oxide.

Still yet another object of the present invention is to provide a new glow in the dark toilet bowl disinfectant composition that flourescently illuminates the water in the toilet bowl so that the toilet bowl is visible in low light and night conditions.

Even still another object of the present invention is to provide a new glow in the dark toilet bowl disinfectant composition that provides a easily discernable visible indicator for indicating when the toilet bowl disinfectant composition is depleted and needs to be replaced. All a user has to do is to check to see if the water in the toilet bowl is fluorescent, if it is not, then it is time to replace the toilet bowl disinfectant composition.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Generally, the glow in the dark toilet bowl disinfectant composition comprises a water soluble ammonia-based disinfectant combined with amounts of strontium sulfide, barium sulfide, lithium fluoride, samarium oxide and cerium oxide.

In closer detail, the toilet bowl disinfectant composition comprises a water soluble ammonia-based disinfectant having sufficient water solubility so that an effective amount of disinfectant for disinfecting a toilet bowl is dissolved in a volume of water of a filled water tank of the toilet. The toilet bowl disinfectant composition also comprises equal parts by volume of strontium sulfide (to provide fluorescence), barium sulfide (to increase the brightness of the fluorescence), lithium fluoride (a material for permitting the ingredients of the disinfectant to be fusible together), and samarium oxide and cerium oxide (both serving as electron traps).

Figure 1:
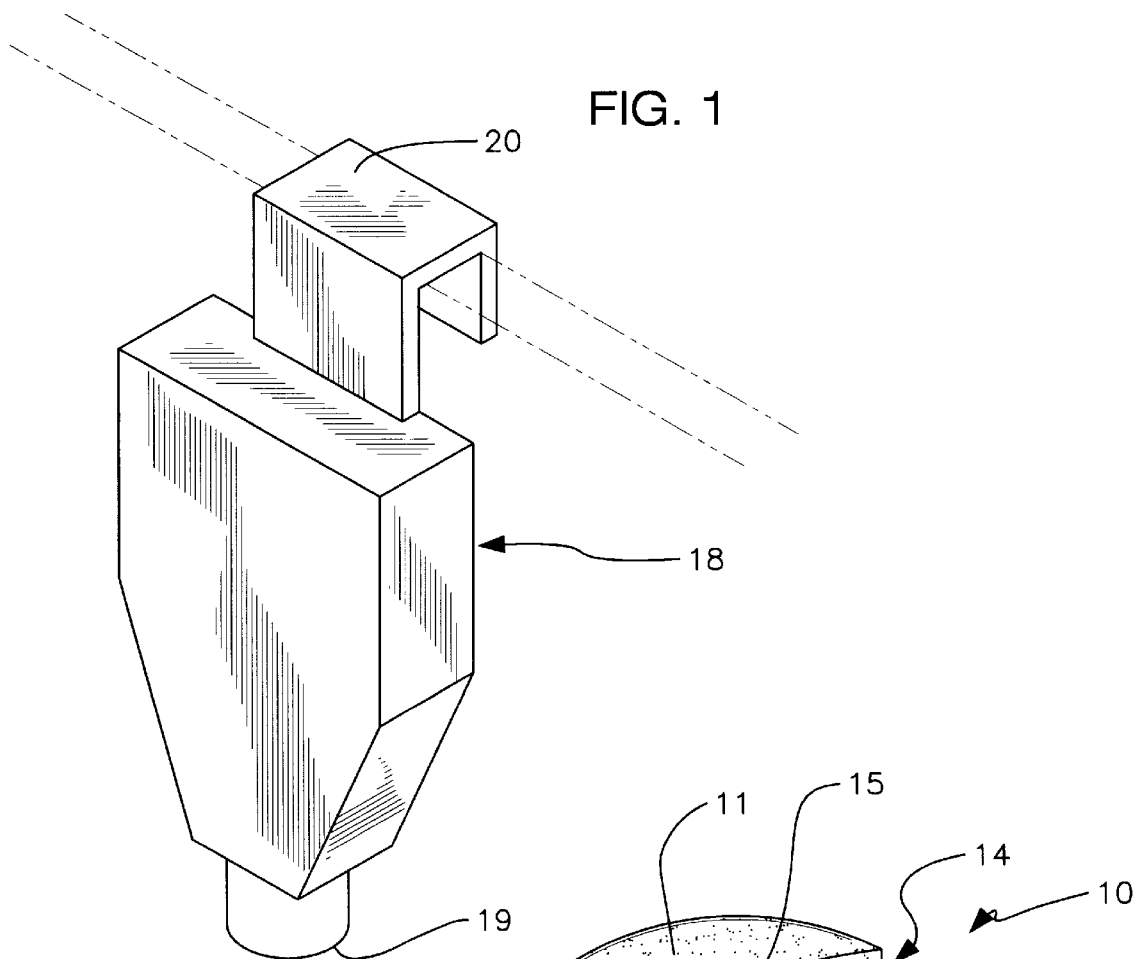
FIG. 1 is a schematic perspective view of a container for holding a water solution embodiment of a new glow in the dark toilet bowl disinfectant composition.
Figure 2:
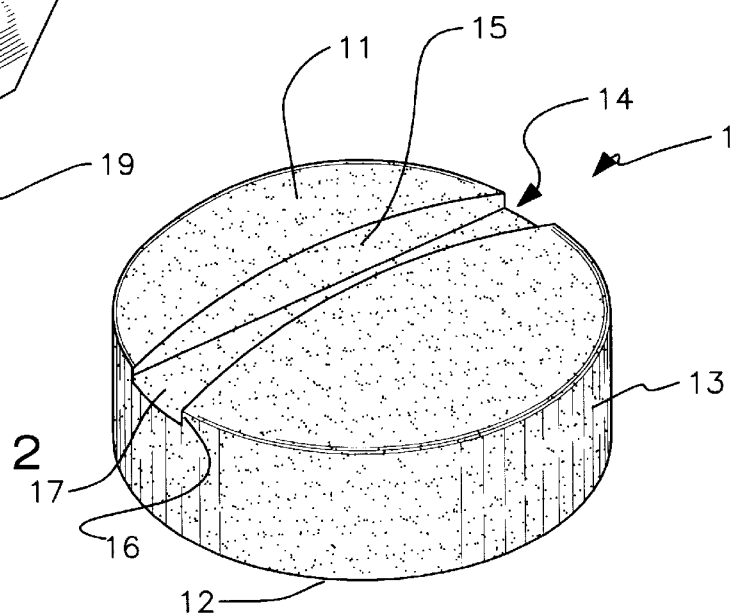
FIG. 2 is a schematic perspective view of the tablet form of the present invention.

The composition may be formed into a generally disk-shaped tablet 10 as illustrated in FIG. 2 having a dome shaped upper face 11, a circular lower face 12 and a cylindrical side wall 13. The upper face of the tablet preferably has a generally rectangular-U-shaped channel 14 extending across a diameter of the upper face. The channel has a spaced apart pair of substantially parallel sides 15,16 and a bottom 17 connecting the sides of the channel together and extending substantially perpendicular to the sides of the channel.

In another preferred embodiment, the composition may be provided in a water solution in a container 18 having lower opening 19 and an upper hook 20. The upper hook is designed for hanging over a side of a toilet tank 21 so that the lower opening of the container is submerged in water held by the toilet tank when the toilet tank is substantially filled. This way the water solution of the composition is in fluid communication with the water in the toilet tank to permit mixing of the composition with the water in the toilet tank.

The toilet bowl disinfectant composition is preferably prepared by first combining the water soluble ammonia-based disinfectant with equal parts by volume of strontium sulfide, barium sulfide, lithium fluoride, samarium oxide and cerium oxide. Second, the combined components are heated to a fusing temperature at which the components are fused together. Third, the fused components are ground into a particulate form which is then re-heated to a temperature slightly less than the fusing temperature to repair crystal surface of the fused material. Finally, the heated particulate form is suspended in a liquid medium such as water.

In use, the glow in the dark toilet bowl disinfectant composition flourescently illuminates the water in the toilet bowl so that the toilet bowl is visible in low light and night conditions. This makes it easy for users to easily discern when the toilet bowl disinfectant composition is depleted and needs to be replaced. All a user has to do is to check to see if the water in the toilet bowl is fluorescent. If it is not, then it is time to replace the toilet bowl disinfectant composition.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

I claim:

1. A toilet bowl disinfectant composition, comprising:

a water soluble ammonia-based disinfectant; and amounts of strontium sulfide, barium sulfide, lithium fluoride, samarium oxide and cerium oxide.

2. The toilet bowl disinfectant of claim 1, wherein strontium sulfide, barium sulfide, lithium fluoride, samarium oxide and cerium oxide are present in equal amounts by volume.

3. The toilet bowl disinfectant composition of claim 1, wherein said composition is formed into a generally disk-shaped tablet having a dome shaped upper face, a circular lower face and a cylindrical side wall, said upper face of said tablet having a generally rectangular-U-shaped channel extending across a diameter of said upper face, said channel having a spaced apart pair of substantially parallel sides and a bottom connecting said sides of said channel together and extending substantially perpendicular to said sides of said channel.

4. A method of preparing a toilet bowl disinfectant composition, comprising the acts of:

combining a water soluble ammonia-based disinfectant with equal parts by volume of strontium sulfide, barium sulfide, lithium fluoride, and, samarium oxide and cerium oxide;

heating the combined components to a fusing temperature at which the components are fused together;

grinding the fused components into a particulate form;

heating the particulate form to a temperature slightly less than said fusing temperature; and suspending the heated particulate form in a liquid medium.

* * * * *